(12) United States Patent
Osborne

(10) Patent No.: US 8,043,232 B2
(45) Date of Patent: Oct. 25, 2011

(54) HIGH PERFORMANCE WIRE GUIDE

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 517 days.

(21) Appl. No.: 11/496,882

(22) Filed: Jul. 31, 2006

(65) Prior Publication Data

US 2007/0049847 A1 Mar. 1, 2007

Related U.S. Application Data

(60) Provisional application No. 60/705,810, filed on Aug. 5, 2005.

(51) Int. Cl.
*A61B 5/00* (2006.01)

(52) U.S. Cl. ........................................ 600/585; 604/527

(58) Field of Classification Search .................. 600/585; 604/527
See application file for complete search history.

(56) References Cited

U.S. PATENT DOCUMENTS

| | | | | |
|---|---|---|---|---|
| 5,065,769 A | * | 11/1991 | de Toledo | 600/585 |
| 5,520,194 A | | 5/1996 | Miyata et al. | |
| 5,728,042 A | * | 3/1998 | Schwager | 600/3 |
| 5,776,100 A | * | 7/1998 | Forman | 604/102.03 |
| 5,827,201 A | * | 10/1998 | Samson et al. | 600/585 |
| 5,897,819 A | | 4/1999 | Miyata et al. | |
| 5,910,364 A | | 6/1999 | Miyata et al. | |
| 6,139,511 A | * | 10/2000 | Huter et al. | 600/585 |
| 6,217,526 B1 | * | 4/2001 | Frassica | 600/585 |
| 6,217,595 B1 | * | 4/2001 | Shturman et al. | 606/159 |
| 6,306,105 B1 | * | 10/2001 | Rooney et al. | 600/585 |
| 6,423,012 B1 | | 7/2002 | Kato et al. | |
| 6,648,837 B2 | | 11/2003 | Kato et al. | |
| 6,685,696 B2 | | 2/2004 | Fleischhacker et al. | |
| 6,702,762 B2 | | 3/2004 | Jafari et al. | |
| 6,805,676 B2 | | 10/2004 | Klint | |
| 2001/0021831 A1 | * | 9/2001 | Fleischhacker et al. | 604/264 |
| 2004/0123915 A1 | * | 7/2004 | Jalisi | 140/71 R |
| 2005/0054951 A1 | * | 3/2005 | Parins | 600/585 |

\* cited by examiner

*Primary Examiner* — Max Hindenburg
*Assistant Examiner* — Renee Danega
(74) *Attorney, Agent, or Firm* — Brinks Hofer Gilson & Lione

(57) ABSTRACT

A high performance wire guide is disclosed, having a core wire and an outer member disposed about the core wire for enhanced torque transmission along a longitudinal length of the core wire. The outer member may be an outer coil wrapped around the core wire in an interference fit.

20 Claims, 6 Drawing Sheets

HIGH PERFORMANCE WIRE GUIDE

CROSS-REFERENCE TO RELATED APPLICATION

This patent application claims the benefit under 35 U.S.C. §119(e) of U.S. provisional patent application Ser. No. 60/705,810, filed Aug. 5, 2005 and entitled HIGH PERFORMANCE WIRE GUIDE, the entire contents of which are incorporated herein by reference.

BACKGROUND OF THE INVENTION

1. Field of the Invention

This invention relates to wire guides used in diagnostic and interventional medical procedures. More specifically, this invention relates to wire guides used for access to complex distal anatomy for diagnostic and interventional procedures.

2. Related Technology

Wire guides (also known as guide wires) have been used in percutaneous entry procedures for diagnostic X-Ray studies and interventional procedures since about the 1950's when the idea of percutaneous, wire guided entry into the vasculature was conceived. A wire guide is typically inserted percutaneously into a body vessel and advanced within the body vessel to a desired location. A catheter is then positioned over the wire guide, inserted into the body vessel percutaneously, and advanced along the wire guide to a desired location.

In order to negotiate the potentially-winding path of the body vessel and to reduce potential damage to the body vessel walls while the wire guide is being advanced, the wire guide preferably has a relatively flexible tip. Also, to further prevent the wire guide from becoming stuck within the body vessel, the wire guide is preferably rotated while being advanced along the body vessel. For example, the rotating distal tip may naturally migrate forward via contact with the body vessel internal walls and static friction forces generated from the contact. More specifically, the rotating movement of the distal tip may cause the wire guide to "walk out of" a depression or a bend in the body vessel. Therefore, to promote rotation of the distal portion of the wire guide upon rotation of the proximal portion by the medical professional, the wire guide preferably has a generally efficient torque transfer between the proximal portion and the distal portion of the wire guide.

Additionally, to improve the pushability and control of the catheter along the body vessel, the wire guide shaft that the catheter is advanced thereover preferably has a relatively high axial stiffness compared to the flexible tip and has a general resistance to kinking or bending so that the wire guide will not become kinked or bent during use. For example, the wire guide shaft preferably has an axial stiffness that is sufficient to prevent the wire guide from folding over itself and becoming obstructed within the body vessel.

However, current wire guide configurations have a number of disadvantages. A small diameter wire guide made from different materials results in several end to end type joints, or joints with sudden diameter changes or both. As a result, areas or points along the length of the wire guide have potentially-dramatic behavior changes, such as in terms of flexibility, kink resistance and diameter. These points can act as obstructions and interfere with advancement of small, fragile catheters. Furthermore, the end to end joints between nitinol and stainless steel can also result in sudden, localized flex points in the stiffer body portion of the wire guide. Flex points are the points at the ends of the splice cannula with sudden changes in stiffness, where the wire guide may kink or bend much easier than the portions of the wire just proximal and just distal to the splice.

One design used to mitigate effects of the steps and kink points utilizes a cannula positioned over a nitinol core wire for the shaft portion of the wire and includes a coil section that abuts the distal end of the cannula to form a smooth outer diameter wire guide. However, the combination of a nitinol core wire and stainless steel cannula has dramatically reduced torque control and kink resistance as compared to a solid nitinol mandrel and dramatically reduced stiffness and pushability as compared to a solid stainless steel mandrel.

Another design used to mitigate effects of the steps and kink points utilizes a coil over the shaft portion of the wire guide. Butt joints are then made between the various coil sections. However, this design does not effectively transfer torque between the proximal and the distal ends of the wire guide. More specifically, when the operator rotates the proximal portion of the wire guide, the coil rotates independently from the core wire and the rotation is not transmitted to the distal tip of the wire guide.

It is therefore desirous to provide a wire guide that maintains a generally constant diameter and that minimizes flex points along the wire guide, while preserving and improving the shaft torque transmission qualities, kink resistance, and stiffness.

BRIEF SUMMARY OF THE INVENTION

In one aspect, the present invention provides a high performance wire guide having enhanced torque transmission, kink resistance, and flexibility. The high performance wire guide includes a core wire having a longitudinal length and an outer coil disposed about the core wire in an interference fit therewith along at least a portion of the longitudinal length for enhanced torque transmission along the portion of the longitudinal length.

The core wire may include a proximal portion, a distal portion, and a body portion extending therebetween. The outer coil preferably extends substantially completely along the core wire body portion. Additionally, the body portion of the wire guide may define a substantially constant diameter and the distal portion of the wire guide may have a decreasing radial stiffness along a direction extending away from the core wire body portion.

The outer coil preferably includes a first portion having a first radial stiffness and a second portion having a second radial stiffness less than the first radial stiffness. Furthermore, the outer coil also preferably includes a third portion extending along the core wire distal portion and having a third radial stiffness less than the second radial stiffness. The third portion preferably extends beyond the core wire distal portion to define a wire guide distal portion. Additionally, in one design, a safety wire extends between the core wire distal portion and the wire guide distal portion to prevent the third portion of the outer coil from undesirably extending upon removal of the wire guide from the body vessel. The safety wire and the core wire may be formed as a single, unitary component.

In another aspect of the present invention, the high performance wire guide includes an outer member disposed about the core wire. The outer member defines a free state diameter when separated from the core wire and an expanded diameter that is greater than the free state diameter when disposed about the core wire. The expanded diameter causes a spring force by the outer member onto the core wire and therefore enhances torque transmission along the longitudinal length of the core wire. In one design, the outer member is an outer coil wrapped around the core wire.

In yet another aspect, the coil includes a first coil disposed about a proximal portion of the core wire in an interference fit with the core wire for enhanced torque transmission to the distal end of the core wire. The coil may further include a second coil disposed about the distal portion of the core wire for enhanced kink resistance and flexibility.

In another aspect of the present invention, the wire guide includes a substantially constant outer diameter along the length of the wire guide. For example, the wire guide may include a multi-wire twist cable tube over a core wire, with the coil sections positioned end to end strategically over the core wire so that the joints are located in areas where the core wire can support the joint. As another example, the coil sections may be connected with each other with a bonding agent.

Further objects, features, and advantages of the present invention will become apparent from consideration of the following description and the appended claims when taken in connection with the accompanying drawings.

DETAILED DESCRIPTION OF THE INVENTION

Figure 1:
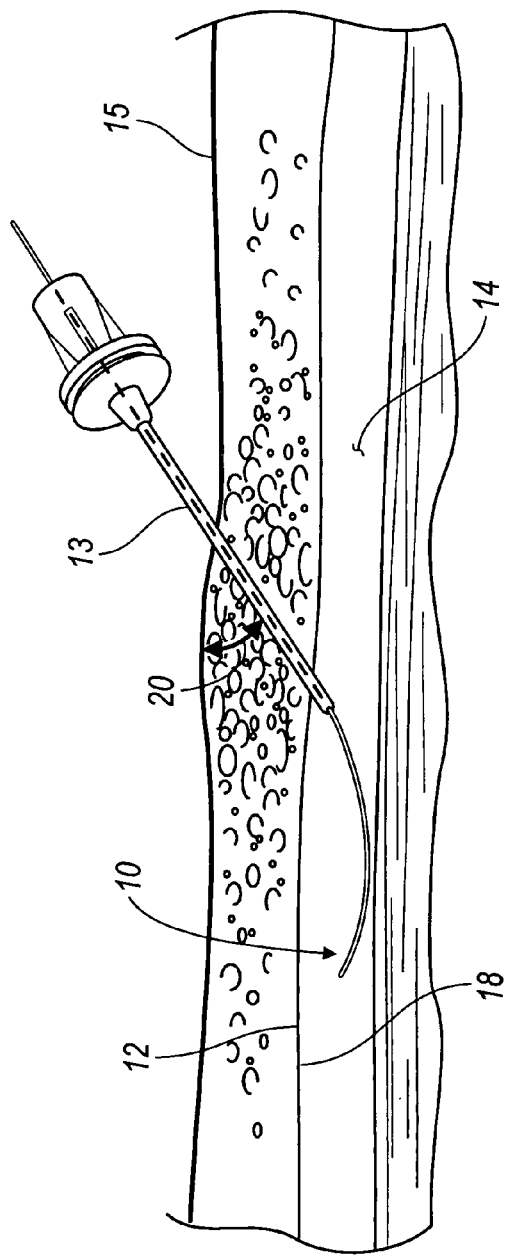
FIG. 1 is a cross-sectional view of body vessel and a high performance wire guide embodying principles of the present invention and being inserted into the body vessel.
Figure 2:
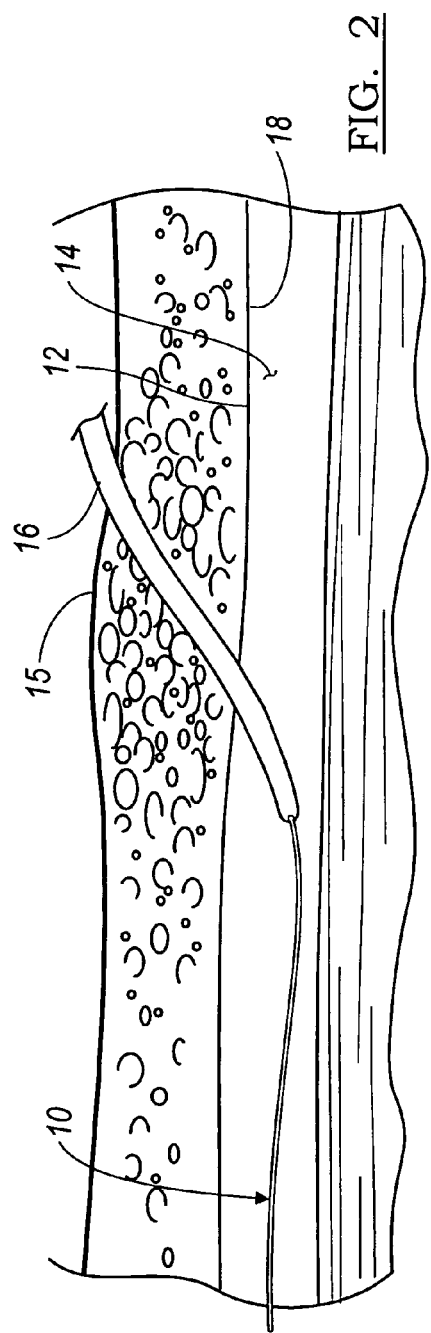
FIG. 2 is a cross-sectional view of a catheter being advanced along the wire guide and into the body vessel shown in FIG. 1.

Referring to FIGS. 1 and 2, a high performance wire guide 10 is shown for percutaneous insertion into a body vessel 12 and guidance of an insertable device along a path and into a conduit 14 of the body vessel 12. For example, an insertable device such as a catheter 16 (FIG. 2) is configured to receive the wire guide 10 and travel along the path, which is defined by the longitudinal axis of the wire guide 10.

More specifically, as shown in FIG. 1, a hollow needle 13 pierces the patient's skin 15 and enters the body vessel 12 at an angle 20 with respect thereto. The wire guide 10 is then inserted into the hollow needle 13 and is advanced into the body vessel 12 and into the conduit 14 to a desired wire guide position. The hollow needle 13 is then pulled in a backward direction so as to be removed from the body vessel 12 and from contact with the wire guide 10. Next, as shown in FIG. 2, the catheter 16 is advanced along the wire guide 10 to a desired catheter position to perform a desired medical procedure. Therefore, the wire guide 10 must be able to be advanced along the conduit 14 and must be able to negotiate any bends or other direction changes within the body vessel 12 between the point of insertion into the body vessel 12 and the desired wire guide position.

Figure 3:
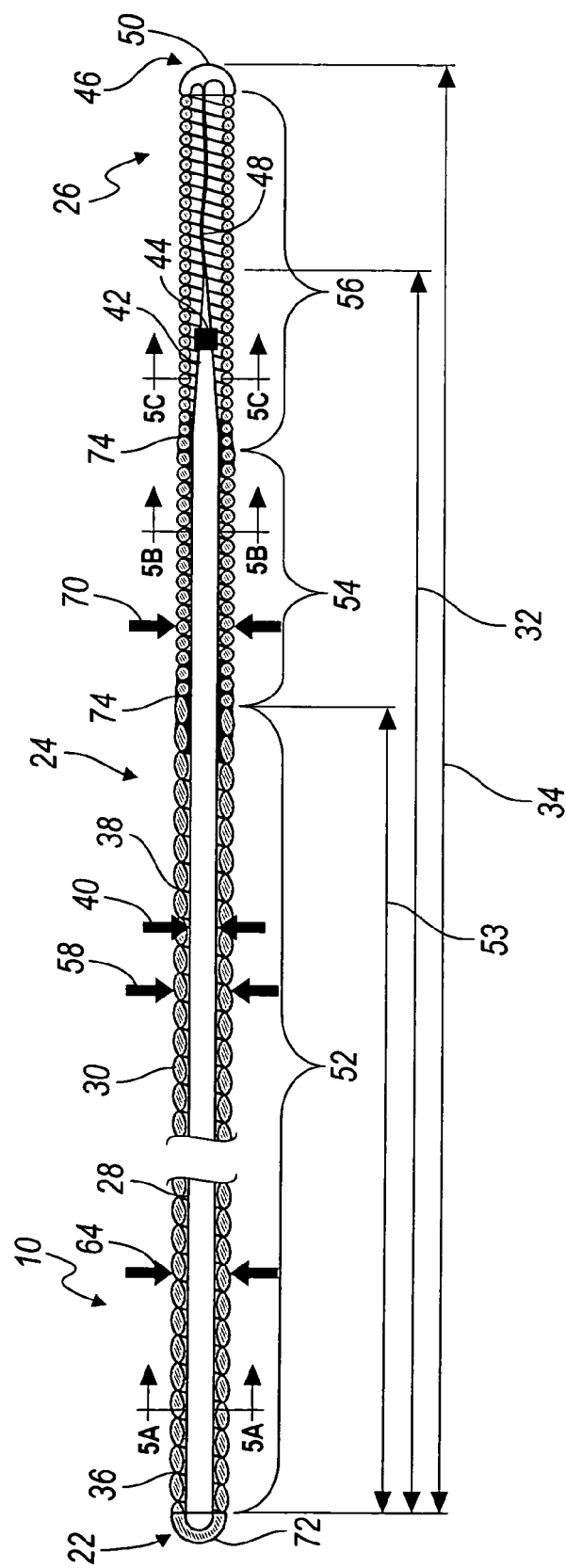
FIG. 3 is a partial cross-sectional view of the wire guide shown in FIG. 1, which includes a core wire and an outer coil disposed therearound.

Referring now to FIG. 3, the wire guide 10 is generally longitudinally divided into three portions: a wire guide proximal portion 22 that preferably remains outside of the body vessel 12 at all times so that it may be gripped and/or controlled by a medical professional performing the medical operation; a wire guide intermediate portion 24 that is generally stiff to permit the advancement of the wire guide 10; and a wire guide distal portion 26 that is first inserted into the body vessel 12 and that is generally flexible to permit negotiation through the winding body vessel 12. Additionally, the wire guide 10 generally includes two components: a core wire 28 that provides general axial stiffness to improve the pushability of the wire guide 10 and an outer member, such as an outer coil 30, to increase axial stiffness, while permitting radial flexibility, and to improve the gripability and the torqueability of the wire guide 10.

The core wire 28 is centrally-located within the wire guide 10 and extends substantially completely along the length thereof. For example, the core wire 28 in the design shown in FIG. 3 extends along a longitudinal length 32 that is slightly less than the longitudinal length 34 of the wire guide 10. More specifically, the core wire 28 extends along all but the distal portion 26 of the wire guide 10 so that the distal portion 26 is generally flexible and is able to negotiate the bends in the body vessel 12. In one exemplary design, the core wire 28 extends along all but the distal 2 to 10 centimeters of the wire guide 10.

The core wire 28 includes a core wire proximal portion 36 that preferably extends to the end of the wire guide proximal portion 22 to improve the gripability and torqueability of the wire guide proximal portion 22 for the medical professional. The core wire 28 also includes a core wire body portion 38 that has a relatively constant diameter 40 and a relatively constant stiffness. Finally, the core wire 28 also includes a core wire distal portion 42 that is generally tapered to create a stiffness transition between the relatively stiff wire guide intermediate portion 24 and the relatively flexible wire guide distal portion 26. For example, the core wire distal portion 42 is tapered to decrease in diameter in a direction extending away from the core wire body portion 38. This figure shows a simple, linear taper but any other suitable design may be used, as is discussed in more detail below.

Figure 6:
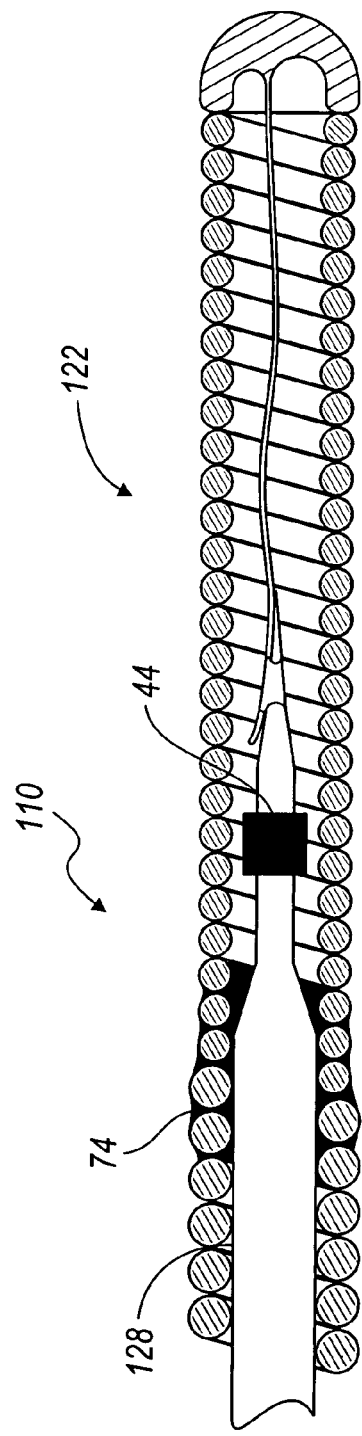
FIG. 6 is an enlarged, partial cross-sectional view of the distal portion of another embodiment of the wire guide, where the distal portion of the core wire has a stepped portion.

The core wire distal portion 42 also preferably includes a radiopaque reference marker 44 to aid the medical professional in controlling the wire guide 10. For example, as shown in FIGS. 3 and 6, small, thin bands of dense metal are added to the core wire distal portion 42 to serve as radiopaque reference markers 44. More specifically, the bands of dense metal are visible within a patient's body via a fluoroscope or an X-ray machine, thereby allowing the medical professional to track the progress of the wire guide 10 during the medical procedure. As an example, the radiopaque reference marker 44 in the figures is placed exactly 4 centimeters from the distal tip 46 of the wire guide 10 so the medical professional has a dimensional reference on the fluoroscope or X-ray films that can be used as an aid in tracking the progress of the wire guide 10 and in selecting stent sizes. The radiopaque reference marker 44 metal bands are preferably formed of gold, tungsten or platinum materials.

The core wire 28 of the wire guide 10 is preferably formed from a "memory material" that maintains its original shape after being bent or deflected. For example, the core wire 28 is preferably a nickel titanium material, such as nitinol. The core wire 28 may also be "doped" or have small amounts of other elements added to enhance its stiffness or kink resistance. The core wire 28 is preferably in an austenitic condition and a superelastic state at room temperature. The core wire distal portion 42 may be tapered by centerless grinding, to any configuration desired, to provide the flex and transition characteristics needed for a particular procedure, as is discussed in more detail below. The core wire 28 preferably has a diameter of approximately 0.007 inches, but may have any other suitable diameter.

A safety wire 48 may connect the core wire distal portion 42 with the wire guide distal tip 46 to prevent an undesirable extension of the wire guide distal portion 26 during a medical procedure. For example, during extraction of the wire guide 10 from the body vessel 12, the safety wire 48 prevents the wire guide distal tip 26 from becoming snagged on a body vessel surface and undesirably elongating. The safety wire 48 shown in FIGS. 3 and 6 is connected to the core wire distal portion 42 by a bonding agent, such as an adhesive, a soldering material, or a brazing material (such as a coating on the surface of the components), but any other suitable connection may be used. Additionally, a rounded end cap 50 defines the distal tip of the safety wire 48 shown in FIGS. 3 and 6 to define the distal tip 46 of the wire guide 10. More specifically, the safety wire 48 and the end cap 50 shown in FIGS. 3 and 6 are unitarily formed with each other to form a single, unitary component. The end cap 50 is preferably generally hemispherical and has a relatively smooth surface to avoid becoming stuck within the body vessel 12. The end cap 50 is connected to the distal end of the outer coil 30 by any suitable method, such as welding, fastening, or adhering. As another alternative, the end cap 50 and the safety wire 48 may be directly formed by soldering, welding, or any other suitable method.

Figure 5A:
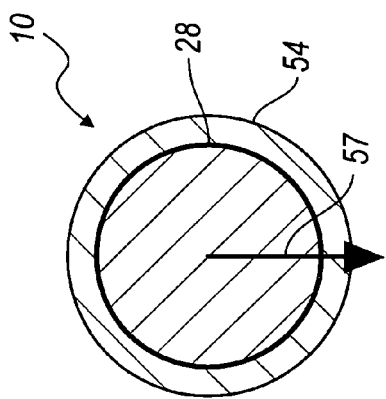
FIGS. 5a through 5c are cross-sectional views taken along lines 5a-5a, 5b-5b, and 5c-5c respectively in FIG. 3.
Figure 5B:
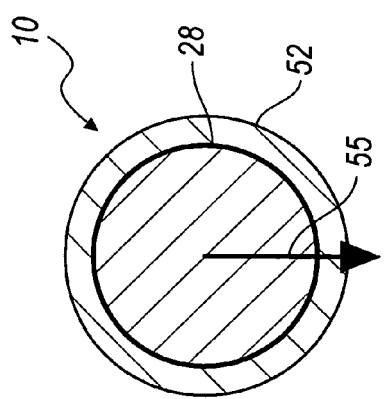
Figure 5C:
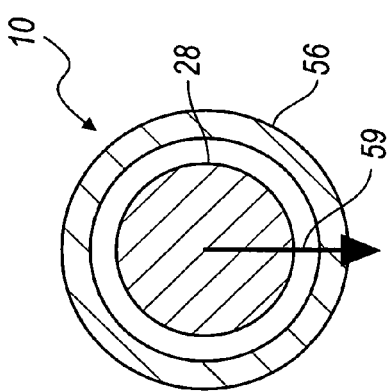

The outer coil 30 includes three longitudinally-extending coils: a torque transfer coil 52 extending from the wire guide proximal portion 22 along a substantial portion 53 of the length of the core wire body portion 38; a transition coil 54 extending from the torque transfer coil 52 to a point adjacent to the core wire distal portion 42; and a lead coil 56 extending from the transition coil 54 to the wire guide distal tip 46. Each of the three coils 52, 54, 56 abuts the adjacent coil(s) so as to cooperate with each other to define a generally constant wire guide diameter 58, thereby creating a relatively smooth outer surface for contacting the body vessel 12. Furthermore, each of the three coils 52, 54, 56 is positioned along a portion of the wire guide 10 having a particular radial stiffness. More particularly, referring to FIGS. 5a through 5c, the torque transfer coil 52 is positioned along a portion of the wire guide 10 having a first radial stiffness 55, the transition coil 54 is positioned along a portion of the wire guide 10 having a second radial stiffness 57, and the lead coil 56 is positioned along a portion of the wire guide 10 having a third radial stiffness 59. The first radial stiffness 55 is greater than the second radial stiffness 57 and third radial stiffness 59, and the second radial stiffness 57 is greater than the third radial stiffness 59, as will be discussed in more detail below.

Figure 4:
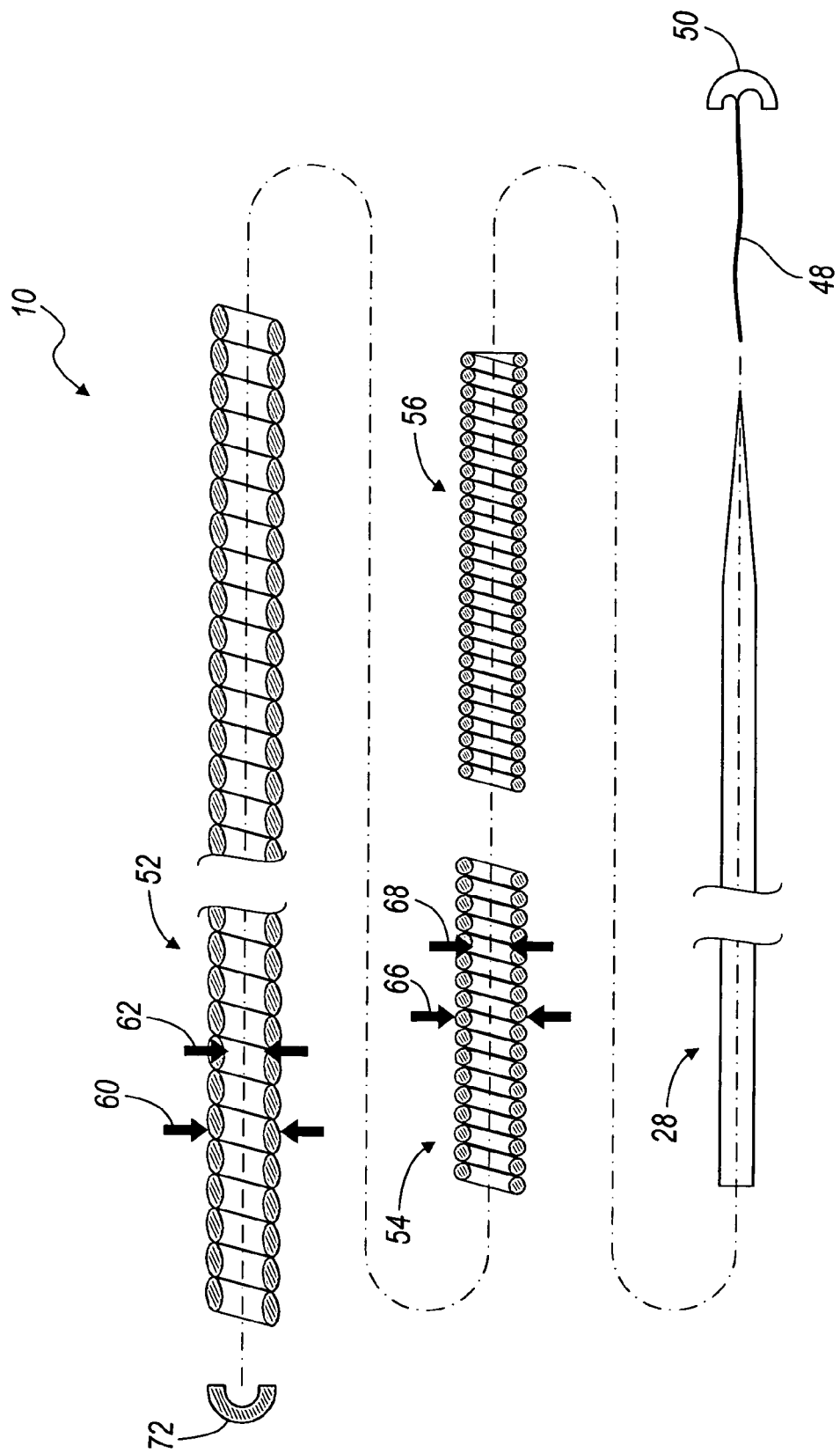
FIG. 4 is an exploded view of the high performance wire guide shown in FIG. 1.

The torque transfer coil 52 is a tightly wound cable that adds considerably to the ability of the wire guide 10 to transmit torque from the proximal portion 22 to the distal end 46 thereof. The torque transfer coil 52 can also bend without taking a permanent set and adds the needed stiffness to the wire guide intermediate portion 24. To further promote the torque transfer properties of the wire guide 10, the outer coil 30 is disposed about the core wire 28 in an interference fit so that a rotational force applied to the outer coil 30 will be substantially or completely transmitted to the core wire 28. For example, referring to FIG. 4, the torque transfer coil 52 is formed to have a free state outer diameter 60 and a free state inner diameter 62 when no external forces are acting thereon, where the free state inner diameter 62 is smaller than the core wire diameter 40 such that the torque transfer coil 52 is expanded into an expanded state having an expanded diameter 64 (FIG. 3) when disposed around the core wire 28. As an exemplary method of coupling the torque transfer coil 52 to the core wire 28, the interference fit may be achieved between the respective components 28, 52 by "screwing" or rotating the core wire 28 relative to the torque transfer coil 52 in a direction opposite to the direction of the winding on the torque transfer coil 52 as it is inserted, thereby causing the torque transfer coil 52 to expand slightly and accept the insertion of the core wire 28.

Figure 7:
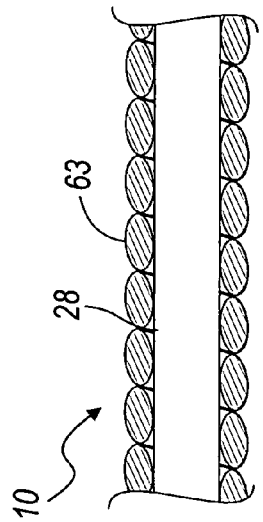
FIG. 7 is an enlarged, partial cross-sectional view of the body portion of another embodiment of the wire guide, where the outer coil is a hollow tube.

The torque transfer coil 52 is preferably formed of stainless steel or MP35N, but any suitable material may be used. The cross-sectional shape of the wire comprising the torque transfer coil 52 preferably has a generally elliptical shape to increase the cross-sectional area (and thereby increase the stiffness) of the torque transfer coil 52 while maintaining an outer diameter equal to that of the intermediate coil 54. Furthermore, as shown in FIG. 7, the torque transfer coil 52 may be formed of a multi-filar tube 63. For example, the torque transfer coil 52 shown in FIG. 7 is a hollow torque cable having an outside diameter of 0.014 inches and an inside diameter of 0.007 inches. The multi-filar hollow tube 63 could be made from 4 strands of stainless steel, MP35N or any suitable material. For example, the four strands may be helically wound to form the hollow cable. Such a cable tube is available from Asahi Intecc Co. Ltd., Newport Beach, Calif.

Similar to the torque transfer coil 52, the intermediate coil 54 is a tightly wound cable that adds considerably to the ability of the wire guide 10 to transmit torque from the proximal portion 22 to the distal end 46 thereof. The intermediate coil 54 can also bend without taking a permanent set and adds the needed stiffness to the wire guide intermediate portion 24. However, the intermediate coil 54 preferably has a stiffness that is relatively lower than that of the torque transfer coil 52 to act as a transition segment between the relatively flexible wire guide distal portion 26 and the relatively stiff wire guide proximal portion 22. The intermediate coil 54 is disposed about the core wire 28 in an interference fit so as to maintain at least a percentage of the torque transfer capabilities of the torque transfer coil 52. For example, referring back to FIG. 4, the intermediate coil 54 is formed to have a free state outer diameter 66 and a free state inner diameter 68 when no external forces are acting thereon, where the free state inner diameter 68 is smaller than the core wire diameter 40 such that the intermediate coil 54 is expanded into an expanded state having an expanded diameter 70 (FIG. 3) when disposed around the core wire 28. As an exemplary method of coupling the intermediate coil 54 to the core wire 28, the interference fit may be achieved between the respective components 28, 54 by "screwing" or rotating the core wire 28 relative to the intermediate coil 54 in a direction opposite to the direction of the winding on the intermediate coil 54 as it is inserted, thereby causing the intermediate coil 54 to expand slightly and accept the insertion of the core wire 28.

The intermediate coil 54 is preferably formed of a stainless steel material, but any suitable material may be used. More preferably, the intermediate coil 54 is made from an 18-8 type, high temper stainless steel wire. The cross-sectional shape of the wire comprising the intermediate coil 54 preferably has a generally circular shape so as to have a stiffness that is relatively less than that of the intermediate coil 54 while having an equal outer diameter 70. The distal end of the intermediate coil 54 preferably ends just proximal to the tapered portion of the core wire 28 such that the portion of the wire guide 10 having the intermediate coil 54 provides an area of initial transition between the relatively stiff wire guide proximal portion 22 and the relatively flexible wire guide distal portion 26, and thereby allows the wire guide distal tip 46 to be advanced further into small, distal vasculature by minimizing sudden, localized, flex points.

Similarly to the intermediate coil 54, the lead coil 56 is a tightly wound cable that defines a portion of the outer surface of the wire guide 10. However, conversely to the intermediate coil 54, the lead coil 56 shown in the figures extends along the tapered portion of the core wire 28 and is spaced apart from the tapered portion of the core wire 28. Therefore, the lead coil 56 is not tightly wound along a substantial length of the core wire 28. For example, the lead coil 56 in FIG. 3 is disposed about and engages the base of the tapered portion, but does not engage the more distal area of the tapered portion. Rather, the lead coil 56 extends in a direction substantially parallel to that of the other respective coils 52, 54 to maintain the generally constant wire guide diameter 58. Additionally, the lead coil 56 preferably has a stiffness that is relatively lower than that of the intermediate coil 54 to negotiate the bends and direction changes within the body vessel 12.

The lead coil 56 is preferably connected to the core wire 28 and or the intermediate coil 54 via a bonding agent, such as an adhesive, a soldering material, or a brazing material. In this embodiment, the lead coil 56 remains in its free state both while unconnected to other components (FIG. 4) and while utilized with the wire guide 10 (FIG. 3). Alternatively, the lead coil 56 is disposed about the base of the tapered portion of the core wire 28 in an interference fit so as to maintain at least a percentage of the torque transfer capabilities of the intermediate coil 54. In this embodiment, only a small portion of the length of the lead coil 56 is radial expanded via contact with the core wire 28, and the remaining portion of the lead coil 56 remains in its free state while utilized with the wire guide 10. The lead coil 56 is preferably coupled with the end cap 50 via a bonding agent or another suitable material. Alternatively, the end cap 50 and the lead coil 56 are formed as a single, unitary component.

The cross-sectional shape of the wire comprising the lead coil 56 preferably has a generally circular shape similar to that of the intermediate coil 54 so as to have an approximately equal outer diameter 70 therewith. The lead coil 56 is preferably formed of a platinum material, but any suitable material may be used. More preferably the lead coil 56 is made from a platinum rhenium alloy (95% Pt 5% Re) wound to the same inner diameter and outer diameter as the torque transfer coil 52 and the intermediate coil 54. The lead coil 56 may alternatively be wound from smaller diameter wire so as to provide the wire guide distal portion 26 with even more flexibility. The lead coil 56 may also be alternatively wound so that the inner diameter and the outer diameter are reduced or attenuated distally to the tip. The pitch of the lead coil 56 could also be changed so as to make it a compression type coil as opposed to an extension type coil. This would have the effect of dramatically increasing the flexibility of the tip coil at the distal tip; potentially further reducing the likelihood of damaging vasculature or dislodging plaque while maneuvering through the vasculature.

The distal end of the torque transfer coil 52 and the proximal end of the intermediate coil 54 preferably butt each other and are joined together via a bonding agent 74 such as an adhesive, a soldering material, or a brazing material. Similarly, the distal end of the intermediate coil 54 and the proximal end of the lead coil 56 preferably butt each other and are joined together via the bonding agent. Also, the distal end of the lead coil 56 and the end cap 50 preferably butt each other and are joined together via the bonding agent and the proximal end of the torque transfer coil 52 is similarly joined to a second end cap 72. This technique joins the respective components 50, 52, 54, 56, 72 with each other while maintaining the generally uniform diameter of the wire guide 10 and providing a smooth, bump free transition and uniform flexibility across the joints. The result of this combination of materials assembled in this way is a uniform, smooth, continuous diameter wire guide with all the necessary transitions and stiffness changes, while maintaining generally uniform flexibility across the joints and providing enough stiffness and torqability to allow precise, smooth manipulation through the vasculature. The length of the bonding agent area along the longitudinal axis of the wire guide 10 is preferably relatively small so that a stiff segment is not present that could interfere with the ability of the wire guide 10 to negotiate small radius turns. More particularly, the length of the bonding agent area is preferably equal to or less than the diameter of the outer coil 30.

The overall length of a typical wire guide 10 shown in the figures is between 140 and 180 centimeters, with the length of the intermediate coil 54 ranging from 5 to 25 centimeters and the length of the lead coil 56 ranging from 2 to 10 centimeters. The designs embodying the principles of the present invention are especially well suited to the smaller wire guides (having a diameter equal to or less than 0.018 inches). In these small diameter wire guides, it is especially challenging to provide a wire guide with the stiffness needed in the shaft portion to make the wire guide pushable and torqable. This is at least one reason why the combination of the torque transfer coil 52, tightly fitted over a nitinol core wire 28, performs so well. The torque transfer coil 52 is therefore preferably a relatively stiff material, with properties similar to stainless steel cannula, but is able to flex without permanent deformation due to its helical construction. Also, since the torque transfer coil 52 is tightly fitted to the core wire 28 and is bonded or soldered to the core wire 28 at both ends, it adds to the torque transmitting characteristics of the core wire 28. This shaft construction, along with the feature of supporting the coil junctions with a full diameter core wire provides a small diameter wire guide with maneuverability, tactile feel and catheter support beyond that of any currently available wire guide.

Figure 8:
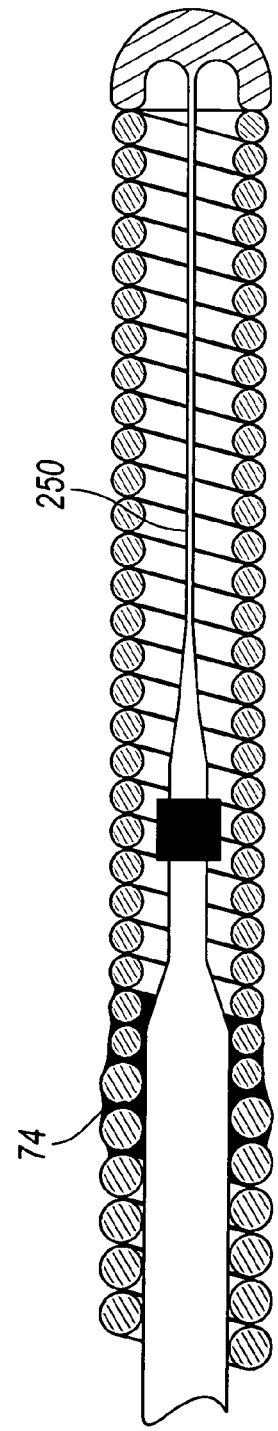
FIG. 8 is an enlarged, partial cross-sectional view of the distal portion of another embodiment of the wire guide, where the core wire and the safety wire are formed as a single, unitary component.

In another embodiment of a wire guide 110 embodying the principles of this invention, FIG. 6 shows a core wire 128 having a first tapered portion 80, a constant diameter portion 82, and a second tapered portion 84. The constant diameter portion 82 provides added stiffness to the wire guide distal portion 122 over the above-described design. As another alternative embodiment, the wire guide 210 shown in FIG. 8 includes a safety wire 250 that is unitarily formed with the core wire 228. The safety wire 250 includes an additional function over that described with respect to the previous figures—the safety wire 250 can be manually deformed before entry into the body vessel such as to retain a particular shape, such as a curve or a J-shape, as needed for the particular procedure and anatomy at the time of use.

Figure 9:
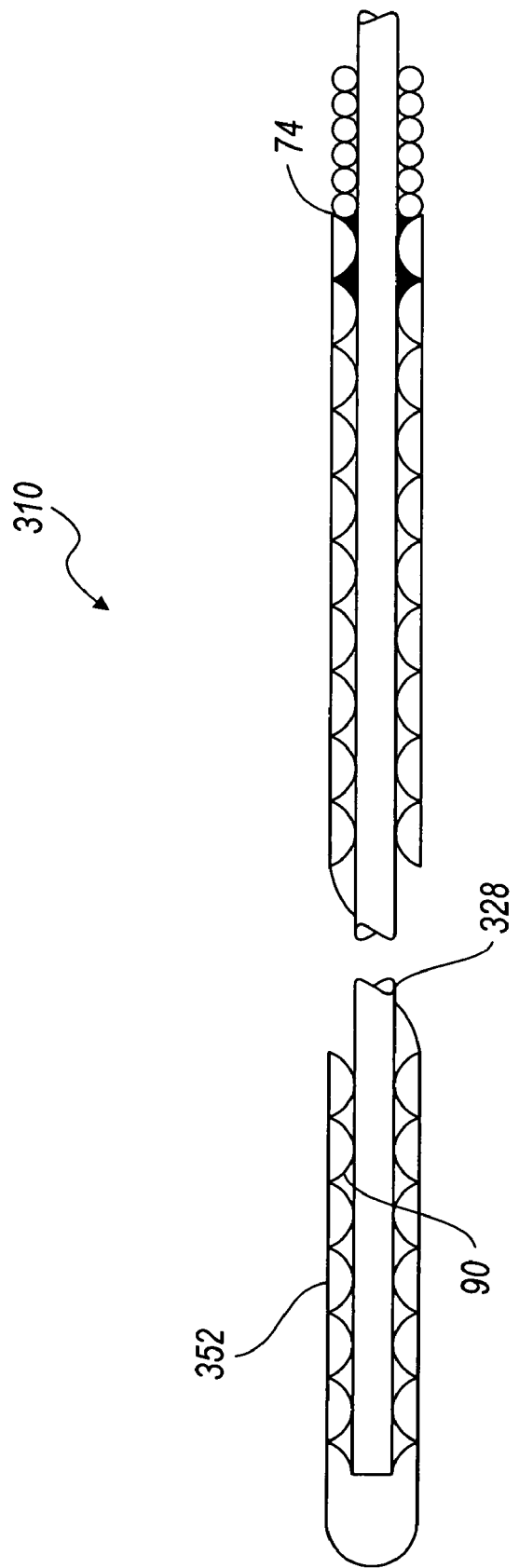
FIG. 9 is an enlarged, partial cross-sectional view of the body portion of yet another embodiment of the wire guide, where the outer coil includes a generally hemispherical cross-section.

In yet another embodiment of a wire guide 310 embodying the principles of this invention, FIG. 9 shows a torque transfer coil 352 that has been ground to have a generally hemispherical cross-section 90. The hemispherical cross-section 90 reduces the outside diameter of the torque transfer coil 352 and makes the outer surface smooth. Additionally, this design makes it possible to use a larger diameter core wire 328. For example, a wire guide 10 as shown in FIG. 3 that is formed with an outside diameter of 0.014 inches using 0.004 inch diameter wire for the torque transfer coil 52 will be able to have a core wire with a diameter of 0.006 inches. However, the wire guide 310 shown in FIG. 9 is able to be initially formed with a torque transfer coil 352 having an outer diameter of 0.018 inches. The outer half of the torque transfer coil 352 is then removed by machining or cutting a portion of the torque transfer coil 352 away until a smooth, flat outer surface is formed and the torque transfer coil 352 has an outer diameter of 0.014 inches and a core wire 328 diameter of about 0.010 inches. The end result would then be a wire guide 352 with a slightly more flexible shaft while still retaining good pushability and torque. Various combinations of cable tube will thickness and core wire diameters can be chosen to modify the wire guide to a particular procedure or anatomy. Centerless grinding can also be used on the intermediate coil and/or the lead coil to reduce the outside diameter thereof and to adjust the flexibility or floppiness of the respective coils.

Of course, many material and dimensional variations could be made within the scope of this invention to produce wire guides with superior properties to access to difficult anatomy. This disclosure only describes a few typical wire guides using the teachings of this disclosure. For example, ordinary, larger, fixed core wire guides could benefit from the feature of having the core wire and the outer wire in an interference fit. This would improve torque transmission and tactile feel dramatically. In addition, many wires today have low coefficient coatings, antibiotic coatings, and antithrombus drug coatings. All these could be applied to the wire guide of this invention.

While the present invention has been described in terms of preferred embodiments, it will be understood, of course, that the invention is not limited thereto since modifications may be made to those skilled in the art, particularly in light of the foregoing teachings.

The invention claimed is:

1. A high performance wire guide including a wire guide proximal end, a wire guide distal end, and a wire guide body portion extending therebetween, the wire guide comprising:
   a core wire having a core wire proximal end, a core wire distal end, and a core wire body portion extending therebetween; and
   an outer coil forming an outer coil lumen, the outer coil disposed about the core wire and the core wire disposed in the outer coil lumen, the outer coil having a cross-section formed of a single layer of wire around the outer coil lumen, the outer coil having an outer coil proximal end disposed about the core wire proximal end defining the wire guide proximal end, the outer coil extending continuously along the core wire body portion to an outer coil distal end disposed distally beyond the core wire distal end, the wire guide distal end defined by the outer coil distal end extending beyond the core wire distal end, wherein the outer coil is disposed about the core wire in an interference fit therewith along the wire guide proximal end and the wire guide body portion, wherein the outer coil includes a first portion having a first radial stiffness and a second portion having a second radial stiffness less than the first radial stiffness.

2. The wire guide of claim 1 wherein the outer coil further includes a third portion extending distally beyond the core wire distal end, wherein the third portion has a third radial stiffness less than the second radial stiffness.

3. The wire guide of claim 2 wherein the first portion and the second portion of the outer coil abut each other and are each coupled to the core wire by a bonding agent.

4. The wire guide of claim 1 wherein the first portion of the outer coil is a multi-filar hollow tube.

5. A high performance wire guide including a wire guide proximal end, a wire guide distal end, and a wire guide body portion extending therebetween, the wire guide comprising:
   a core wire having a core wire proximal end, a core wire distal end, and a core wire body portion extending therebetween; and
   a continuous outer coil disposed about the coil wire, the continuous outer coil having an outer coil proximal end disposed about the core wire proximal end defining the wire guide proximal end, the continuous outer coil extending continuously along the core wire body portion to an outer coil distal end disposed distally beyond the core wire distal end, the wire guide distal end defined by the outer coil distal end extending beyond the core distal end, wherein the continuous outer coil is disposed about the core wire in an interference fit therewith along the wire guide proximal end and the wire guide body portion, the continuous outer coil having a torque transfer coil part extending from the outer coil proximal end and an intermediate coil part longitudinally extending from the torque transfer coil part, the intermediate coil part having a stiffness that is lower than that of the coil part.

6. The wire guide of claim 5 wherein the core wire body portion defines a substantially constant outer diameter.

7. The wire guide of claim 6 wherein the core wire distal end has a decreasing radial stiffness along a direction extending away from the core wire body portion.

8. The wire guide of claim 5 further comprising a safety wire extending between the core wire distal end and the outer coil distal end to substantially prevent elongation of the outer coil.

9. The wire guide of claim 8, wherein the safety wire and the core wire distal end are formed unitarily with each other to form a single, unitary component.

10. The wire guide of claim 5, wherein the core wire distal end is tapered.

11. The wire guide of claim 5 wherein the wire guide defines a substantially constant outer diameter.

12. The wire guide of claim 5 wherein the core wire is formed of shape memory alloy with a transition temperature.

13. The wire guide of claim 5, wherein the torque transfer coil part has a generally elliptical cross-section shape.

14. A high performance wire guide comprising:
   a core wire having a longitudinal length and including a core wire proximal end, a core wire distal end, and a core wire body portion extending continuously therebetween, the wire guide defining first, second, and third radial stiffness along the length of the core wire, the first radial stiffness being greater than the second radial stiffness and the second radial stiffness being greater than the third radial stiffness; and
   an outer member including an outer member proximal end, an outer member distal end, and an outer member body portion extending continuously therebetween, the outer member proximal end disposed about the core wire proximal end defining a wire guide proximal end, the outer member extending continuously along the core wire body portion to an outer member distal end, the outer member distal end extending distally beyond the core wire distal end defining a wire guide distal end, the wire guide having a wire guide body portion extending between the wire guide proximal end and the wire guide distal end, wherein along the wire guide proximal end and the wire guide body portion the outer member defines a free state diameter when separated from the core wire and defines an expanded diameter greater than the free state diameter when disposed about the core wire for enhanced torque transmission along at least a portion of the longitudinal length of the core wire, the outer member including a torque transfer portion that abuts an intermediate portion, the torque transfer portion and the intermediate portion terminating at a first abutment between the torque transfer portion and the intermediate portion, the outer member further including a lead portion that abuts the intermediate portion, the intermediate portion and the lead portion terminating at a second abutment between the intermediate portion and the lead portion, the intermediate portion having a lower stiffness than the torque transfer portion and the lead portion having a lower stiffness than the intermediate portion.

15. The wire guide of claim 14 wherein the outer member is an outer coil wrapped around the core wire.

16. The wire guide of claim 14, wherein the torque portion has a generally elliptical cross-sectional shape.

17. A high performance wire guide comprising:
a core wire including a core wire proximal end, a core wire distal end, and a core wire body portion extending therebetween;
a first coil disposed about the core wire proximal end and extending therefrom along the core wire body portion in an interference fit for enhanced torque transmission to the core wire distal end, the first coil having a first coil distal end; and
a second coil disposed about the core wire distal end and extending distally beyond the core wire distal end for enhanced kink resistance and flexibility, the second coil having a second coil proximal end that is attached to and abuts the first coil distal end, the second coil extending longitudinally from the first coil distal end, the second coil including an intermediate part and a lead part, the intermediate part abutting the first coil at a first abutment, the first coil and the intermediate part terminating at the first abutment, the lead part abutting the intermediate part at a second abutment, the intermediate part and the lead part terminating at the second abutment, the lead part having a lower stiffness than the intermediate part and the intermediate part having a lower stiffness than the first coil.

18. The wire guide of claim 17 wherein the first coil includes a torque transfer portion having a first radial stiffness and a transition portion having a second radial stiffness less than the first radial stiffness.

19. The wire guide of claim 18 wherein the torque transfer portion of the first coil is a multi-filar hollow tube and the transition portion of the first coil is a stainless steel coil.

20. A high performance wire guide including a wire guide proximal end, a wire guide distal end, and a wire guide portion extending therebetween, the wire guide comprising:
a core wire having a core wire proximal end, a core wire distal end, and a core wire body portion extending therebetween; and
an outer coil disposed about the core wire, the outer coil having an outer coil proximal end disposed about the core wire proximal end defining the wire guide proximal end, the outer coil extending continuously along the core wire body portion to an outer coil distal end disposed distally beyond the core wire distal end, the wire guide distal end defined by the outer coil distal end extending beyond the core wire distal end, wherein the outer coil is disposed about the core wire in an interference fit therewith along the wire guide proximal end and the wire guide body portion, the outer coil having a torque transfer coil part extending from the outer coil proximal end and an intermediate coil part longitudinally extending from the torque transfer coil part, the intermediate coil part having stiffness that is lower than that of the torque transfer coil part, the torque transfer coil part having a generally elliptical cross-sectional shape.

\* \* \* \* \*

UNITED STATES PATENT AND TRADEMARK OFFICE
CERTIFICATE OF CORRECTION

| | | |
|---|---|---|
| PATENT NO. | : 8,043,232 B2 | Page 1 of 1 |
| APPLICATION NO. | : 11/496882 | |
| DATED | : October 25, 2011 | |
| INVENTOR(S) | : Thomas A. Osborne | |

It is certified that error appears in the above-identified patent and that said Letters Patent is hereby corrected as shown below:

<u>In the Claims</u>

In column 10, claim 5, line 21, after "beyond the core" insert --wire--.

In column 10, claim 5, line 29, after "than that of the" insert --torque transfer--.

In column 10, claim 13, line 49, after "generally elliptical" replace "cross-section" with --cross-sectional--.

In column 10, claim 14, line 55, before "along the length" replace "stiffness" with --stiffnesses--.

In column 11, claim 16, line 24, after "wherein the torque" insert --transfer--.

In column 12, claim 20, line 18, after "and a wire guide" insert --body--.

In column 12, claim 20, line 37, before "stiffness that is" insert --a--.

Signed and Sealed this
Seventeenth Day of April, 2012

David J. Kappos
*Director of the United States Patent and Trademark Office*